United States Patent
Shaw et al.

(10) Patent No.: US 11,000,217 B2
(45) Date of Patent: May 11, 2021

(54) BLOOD COLLECTION TUBE HOLDER WITH DISCHARGE NEEDLE DISPLACEMENT MEMBER

(71) Applicants: Retractable Technologies, Inc., Little Elm, TX (US); Thomas J. Shaw, Frisco, TX (US)

(72) Inventors: Thomas J. Shaw, Frisco, TX (US); Mark Small, Heavener, OK (US)

(73) Assignee: Retractable Technologies, Inc., Little Elm, TX (US)

( * ) Notice: Subject to any disclaimer, the term of this patent is extended or adjusted under 35 U.S.C. 154(b) by 242 days.

(21) Appl. No.: 15/277,259

(22) Filed: Sep. 27, 2016

(65) Prior Publication Data

US 2018/0008180 A1   Jan. 11, 2018

Related U.S. Application Data

(63) Continuation-in-part of application No. 15/202,118, filed on Jul. 5, 2016.

(51) Int. Cl.
*A61B 5/15*    (2006.01)
*A61B 5/153*   (2006.01)

(52) U.S. Cl.
CPC .... *A61B 5/150732* (2013.01); *A61B 5/15003* (2013.01); *A61B 5/153* (2013.01); *A61B 5/150534* (2013.01); *A61B 5/150885* (2013.01); *A61B 5/150389* (2013.01); *A61B 5/150503* (2013.01); *A61B 5/150572* (2013.01)

(58) Field of Classification Search
None
See application file for complete search history.

(56) References Cited

U.S. PATENT DOCUMENTS

| | | | |
|---|---|---|---|
| 5,810,775 | A | 9/1998 | Shaw |
| RE39,107 | E | 5/2006 | Shaw |
| D645,962 | S | 9/2011 | Shaw et al. |
| D660,420 | S | 5/2012 | Shaw et al. |
| 8,469,927 | B2 | 6/2013 | Shaw et al. |
| 8,496,600 | B2 | 7/2013 | Shaw et al. |
| 9,247,899 | B2 | 2/2016 | Shaw et al. |

(Continued)

FOREIGN PATENT DOCUMENTS

WO    WO 2005087102 A1 * 9/2005   ......... A61B 5/15003

*Primary Examiner* — Matthew Kremer
(74) *Attorney, Agent, or Firm* — Monty L Ross PLLC; Monty L. Ross

(57) ABSTRACT

A medical device configured as a blood collection tube holder, the device having a body with two spaced-apart, oppositely facing, coaxially aligned needles including a forwardly facing venipuncture needle and a rearwardly facing fluid discharge needle, the two needles being held by first and second needle holders separated by a compressible fluid seal defining part of a fluid path between the two needles and the two needle holders. The body also includes a discharge needle displacement member that is manually repositioned following removal of the last blood tube holder so that the discharge needle displacement member contacts the second needle holder and displaces the second needle holder and the fluid discharge needle laterally inside the body to initiate retraction of the venipuncture needle into a rearwardly projecting needle retraction chamber.

3 Claims, 10 Drawing Sheets

(56) References Cited

U.S. PATENT DOCUMENTS

| | | | | |
|---|---|---|---|---|
| 2003/0200812 | A1* | 10/2003 | Kuhn | A61M 1/3639 73/715 |
| 2008/0255523 | A1* | 10/2008 | Grinberg | A61M 5/008 604/192 |
| 2009/0306601 | A1* | 12/2009 | Shaw | A61M 5/158 604/177 |
| 2010/0317999 | A1* | 12/2010 | Shaw | A61B 5/154 600/576 |
| 2015/0073303 | A1* | 3/2015 | Shaw | A61M 5/3232 600/576 |

\* cited by examiner

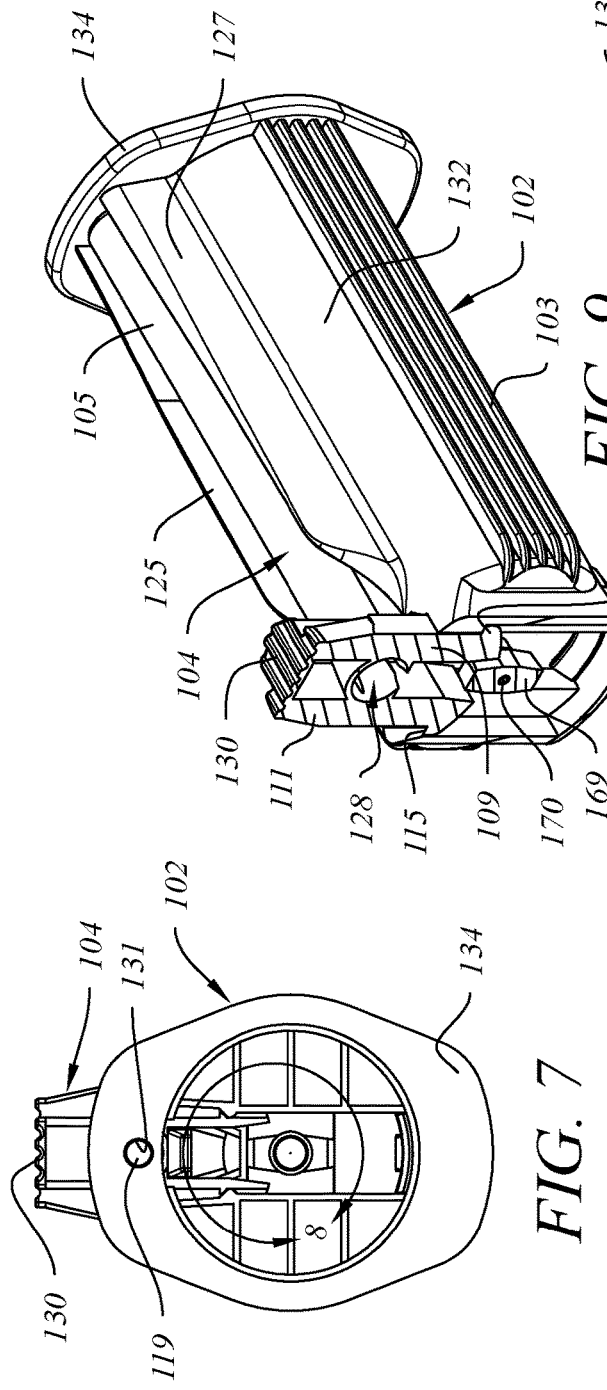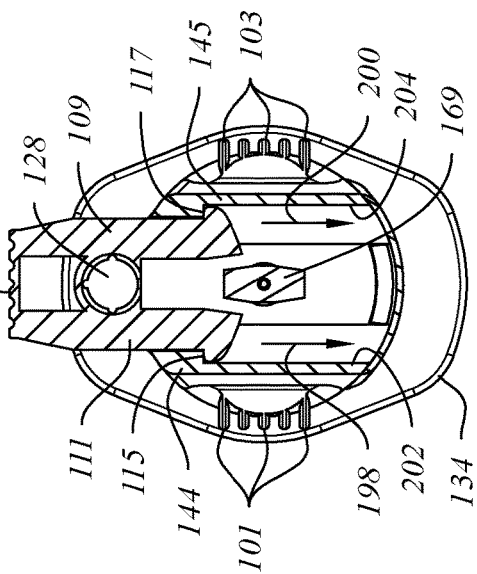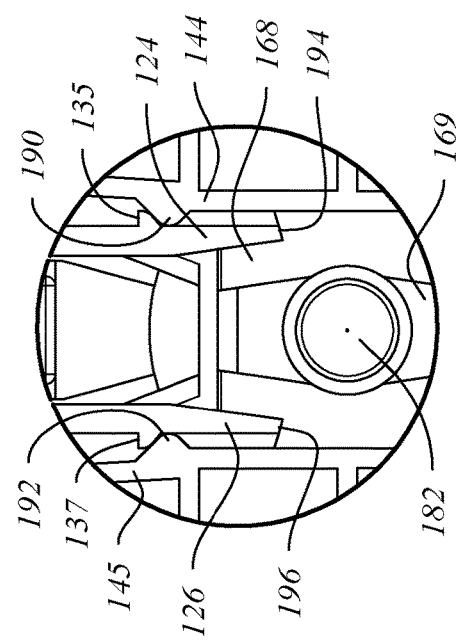

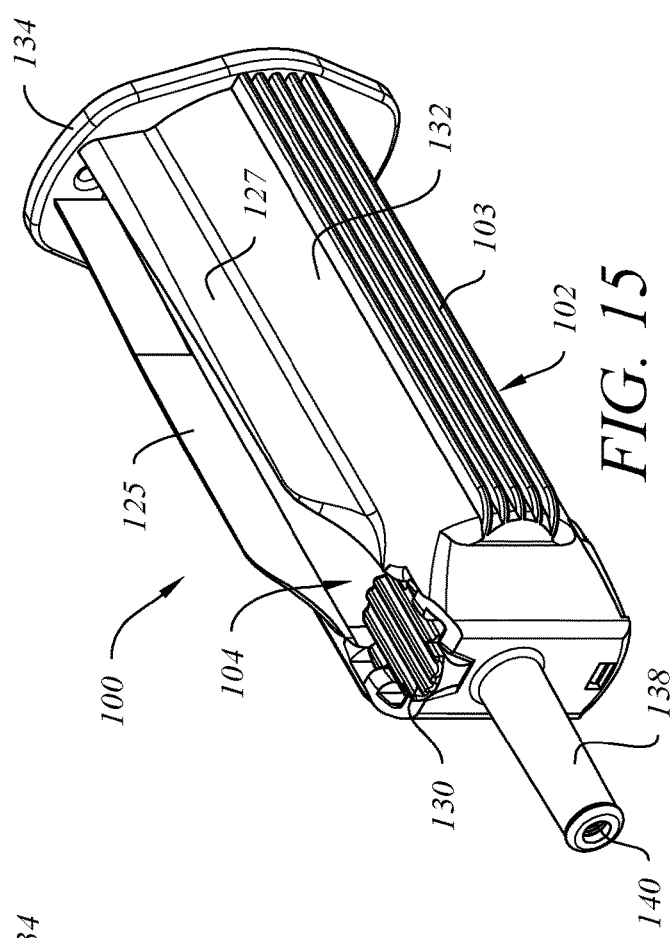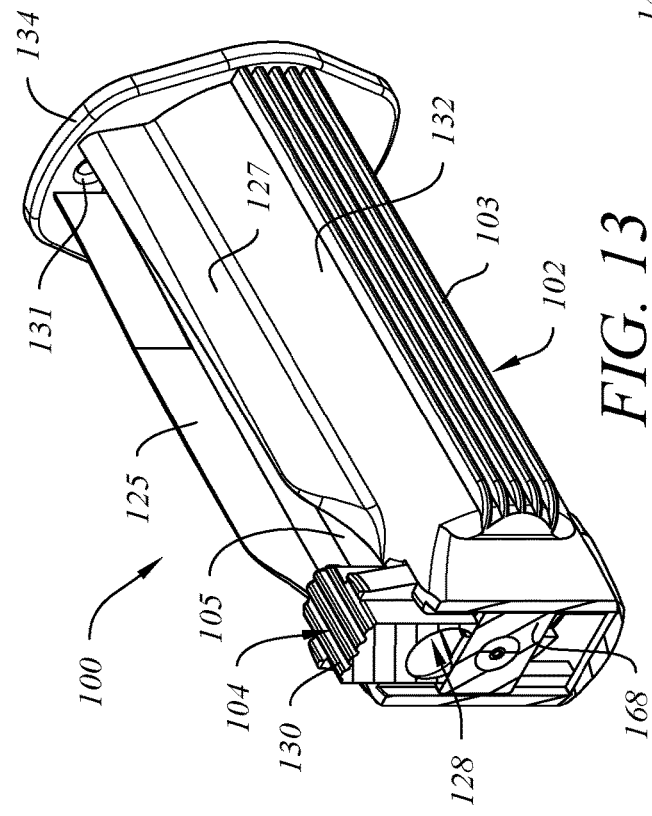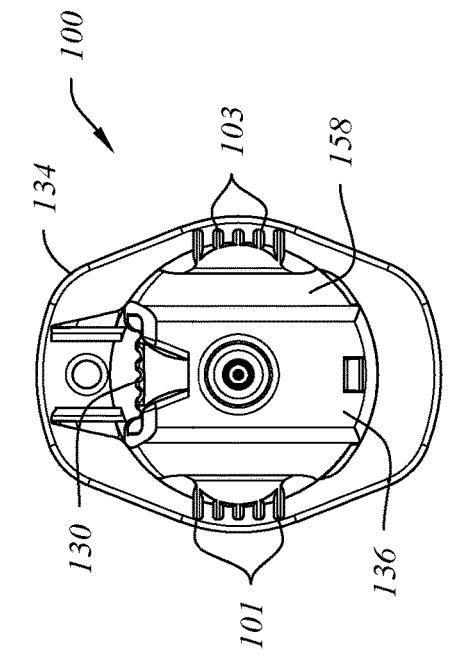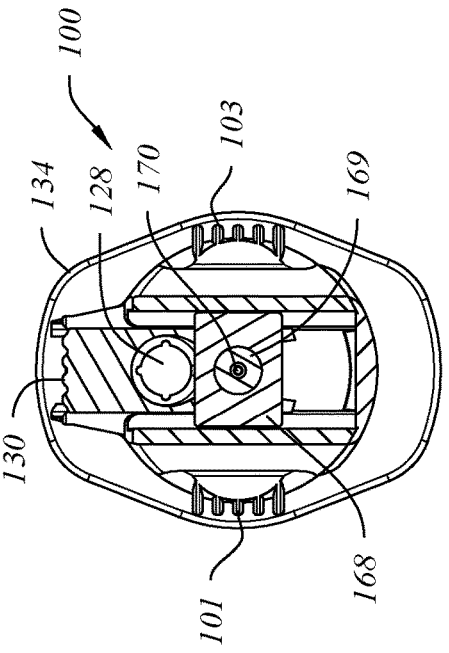

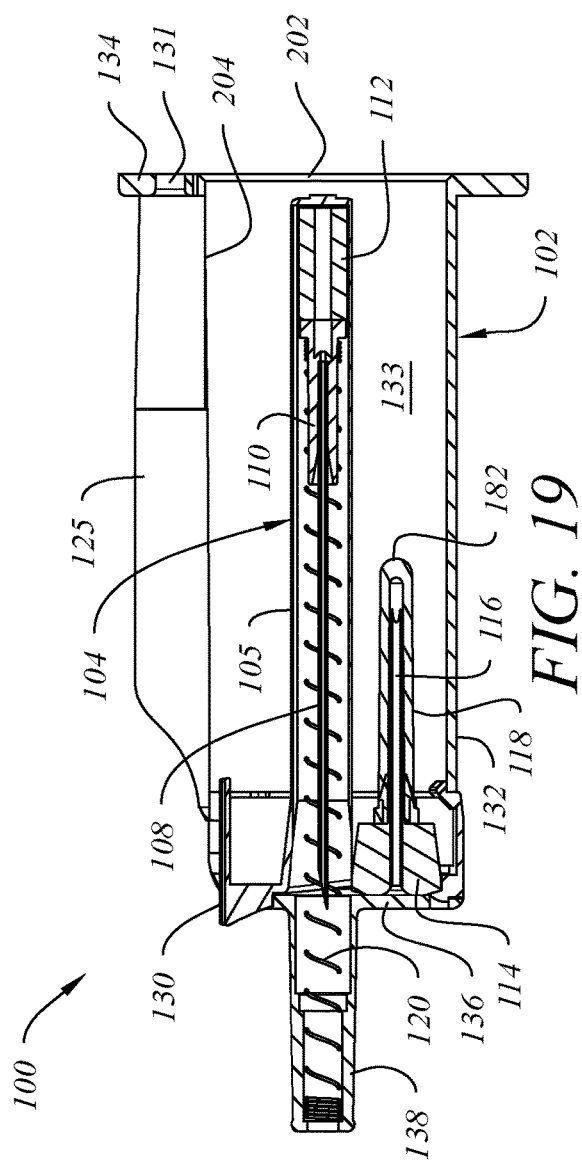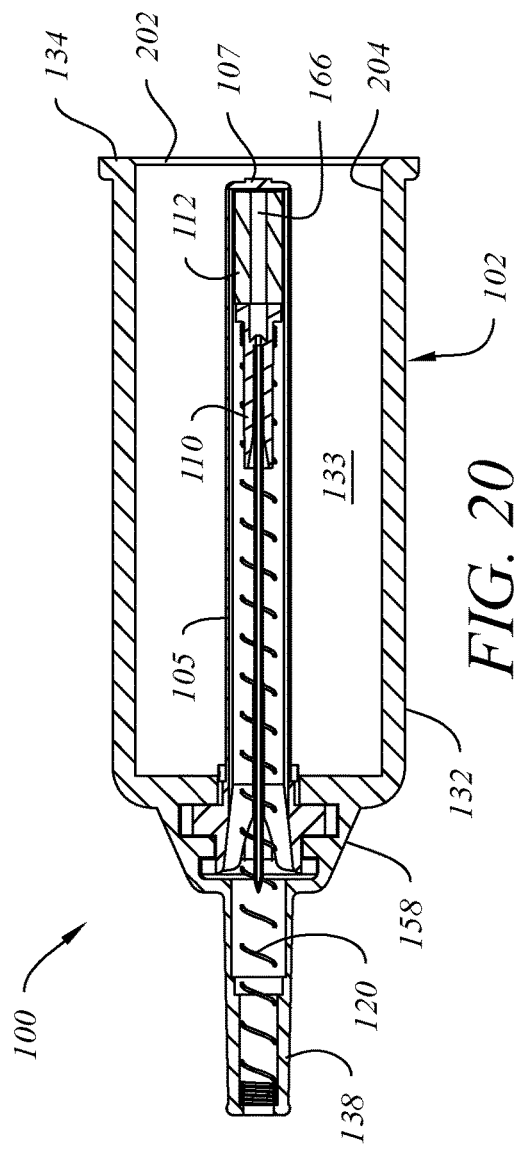

BLOOD COLLECTION TUBE HOLDER WITH DISCHARGE NEEDLE DISPLACEMENT MEMBER

CROSS-REFERENCE TO RELATED APPLICATIONS

This application is a continuation-in-part of U.S. patent application Ser. No. 15/202,118, filed Jul. 5, 2016.

TECHNICAL FIELD

This invention is a medical device, and more particularly, a blood collection tube holder configured for use in drawing and collecting samples of bodily fluids, and especially vascular fluids such as blood. The invention includes a body having two longitudinally separated, oppositely facing, coaxially aligned needles. A venipuncture needle faces forwardly and can be inserted into a patient to withdraw fluid. A discharge needle faces rearwardly and is insertable into the forwardly facing end of a blood collection tube used in conjunction with the subject device. The venipuncture needle is retractable following use and both needles remain inside the body of the device for safe disposal. Use of the device reduces the likelihood of inadvertent needle-stick injuries and contamination of health care workers and others with blood-borne pathogens.

BACKGROUND

U.S. Pat. No. 5,810,775 and RE39,107 disclose Medical devices such as blood collection tube holders having a single double-ended needle that is retractable into the cylindrical body of the tube holder following use. Needle retraction is initiated by closing a hinged cap upon removal of a fluid collection tube, which causes a coaxially aligned inner sleeve to move forwardly and release a rearwardly biased needle.

U.S. D645,962 and U.S. D660,420 disclose a housing for a collection device for bodily fluids that comprises a substantially cylindrical section having a forwardly extending cylindrical nose, an open rear end, a plurality of longitudinally extending ribs disposed on each side of the cylindrical section, and an elongate arm pivotably mounted near the rear of the housing over an upwardly facing slot in the tube holder.

U.S. Pat. No. 8,469,927 discloses a fluid flow control device having an actuator that moves translationally relative to the housing but does not have a rearwardly facing needle and is not disclosed for use with a fluid collection tube insertable into the housing.

U.S. Pat. No. 8,496,600 discloses a non-reusable collection device for bodily fluids such as vascular blood, the device having a housing configured similarly to that of U.S. D645,962, wherein a single, rearwardly biased double-ended needle is constrained prior to needle retraction by a rotatably mounted lug ring. The needle is released during retraction by depressing a pivotably mounted trigger connected to the body of the device to contact and rotate the lug ring, after which the needle holder is driven into a retraction cavity disposed inside the trigger while the trigger is disposed at an angle that intersects the central longitudinal axis through the housing U.S. Pat. No. 9,247,899 discloses a blood draw device with a single, double-ended retractable needle that is similar in form and function to the device of U.S. Pat. No. 8,496,600 except that a retainer clip retains the rearwardly biased double-ended needle until the front portion of an actuator (similar to the trigger of the '600 patent) is pivoted downwardly to cause the retainer clip to release the needle holder, after which a compressed spring expands and drives the needle holder into a retraction cavity inside the actuator that is disposed at an angle that intersects the central longitudinal axis through the housing.

SUMMARY OF THE INVENTION

A medical device is disclosed that is desirably configured as a blood collection tube holder. The subject device satisfactorily comprises a molded plastic body having a generally cylindrical interior space that is configured to receive and engage a stoppered end of a conventional blood collection tube such as those typically used in conjunction with such devices. The device of the invention desirably includes two spaced-apart, oppositely facing, coaxially aligned needles held inside the body. One needle is a forwardly projecting venipuncture needle having a beveled tip suitable for insertion into a vein of a patient. The venipuncture needle is held by a first needle holder that is rearwardly biased, preferably by a compressed spring. The second needle is a rearwardly facing fluid discharge needle that is held by a second needle holder supported inside the body and that is insertable through the stoppered end of a blood collection tube. A cylindrical fluid seal is desirably disposed between the first and second needle holders. The fluid seal has a longitudinally extending passageway that is coaxial with the two needles and defines part of a fluid path between the two needles and the two needle holders. The fluid seal is desirably made of a compressible polymeric material that will resist fluid leakage around the seal when it is compressed slightly during installation between the two needle holders.

The blood collection tube holder also desirably comprises a discharge needle displacement member that slidably engages the body and is used to initiate retraction of the venipuncture needle following collection of a bodily fluid such as blood. As the stoppered end of the blood collection tube separates from the fluid discharge needle following collection of a blood sample, a collapsible protective polymeric sheath disposed around the fluid discharge needle expands to cover the rearwardly facing tip of the fluid discharge needle. The discharge needle displacement member desirably includes a front portion configured to provide sliding engagement with guide members disposed behind the front wall of the body, and also has a rearwardly projecting needle retraction chamber having a forwardly facing open end that is accessed through an opening in the front portion. The front portion of the discharge needle displacement member desirably further includes an outwardly facing, textured touch surface to which pressure is applied manually to initiate transverse sliding movement of the discharge needle displacement member relative to the body after a blood collection tube is withdrawn from the blood collection tube holder.

As the discharge needle displacement member slides further into the body of the device in response to the manually applied pressure, it moves in a direction that is transverse to the fluid flow path through the blood collection tube holder. When the front portion of the discharge needle displacement member contacts the second needle holder, it the second needle holder to disengage from the fluid seal, and displaces the second needle holder and fluid discharge needle to a resting position that is laterally spaced apart from the needle retraction chamber but is still protected inside the body. As the second needle holder and the fluid discharge needle attached to it are moved away from the fluid seal, the forwardly facing opening into the needle retraction chamber is moved into coaxial alignment with the fluid seal, the first needle holder and the venipuncture needle. Once the first needle holder and the needle retraction chamber are coaxially aligned, the fluid seal, the rearwardly biased, first needle holder and the venipuncture needle are propelled rearwardly into the needle retraction cavity. In a preferred embodiment of the invention, the rearwardly directed biasing force is sufficient to withdraw the tip of the venipuncture needle directly from the patient's body and inside the body of the blood collection tube holder, thereby significantly reducing the likelihood of an inadvertent needle stick injury or pathogenic contamination to others.

This section of the application also incorporates by reference into this Summary of the Invention the statements previously made in the section of this patent application subtitled "Technical Field." These and other features, objects and advantages of the present invention will become better understood from a consideration of the following detailed description of the preferred embodiments and appended claims in conjunction with the drawings.

BRIEF DESCRIPTION OF THE DRAWINGS

The system and method of the invention are further described and explained in relation to the following drawings wherein:

FIG. 7 is a rear elevation view of the medical device of FIG. 1;

FIG. 8 is a detail view taken from FIG. 7;

FIG. 9 is a front perspective view as in FIG. 2, with a cross-section taken behind the front wall of the body and through the front part of a discharge needle displacement member;

FIG. 10 is a front elevation view of the device as depicted in FIG. 9;

FIG. 13 is a front perspective view as in FIG. 9, but with the discharge needle displacement member moved into contact with the discharge needle holder prior to retraction of the venipuncture needle;

FIG. 14 is a front elevation view of the device as depicted in FIG. 13;

FIG. 15 is a front perspective view of the device of FIG. 2 after the venipuncture needle is fully retracted;

FIG. 16 is a front elevation view of the device as depicted in FIG. 15;

FIG. 19 is a cross-sectional view taken along line 19-19 of FIG. 17; and FIG. 20 is a cross-sectional view taken along line 20-20 of FIG. 17.

In each drawing figure, the subject device is depicted in an orientation wherein the height of the flange around the rear opening of the device is greater than the width of the flange and the textured touch surface of the discharge needle displacement member faces upwardly relative to the body. Accordingly, the bevel surface of the venipuncture needle is also depicted facing upwardly to facilitate insertion of the needle into a vein of a patient. It should be appreciated by those of skill in the art upon reading this disclosure, however, that some medical personnel may prefer to use the device in an orientation that is rotated 90 degrees around its longitudinal axis, so that the flange is wider that it is high and so that the touch surface of the discharge needle displacement member faces to the side rather than upwardly as shown in the accompanying drawings. Where the subject device is recommended to be used in the second orientation, with the touch surface of the discharge needle displacement member facing to the side, the venipuncture needle will still desirably be installed in the device with the needle bevel facing upwardly (not facing the skin of the patient at the insertion point) as depicted in the accompanying drawings.

DETAILED DESCRIPTION

Figure 1:
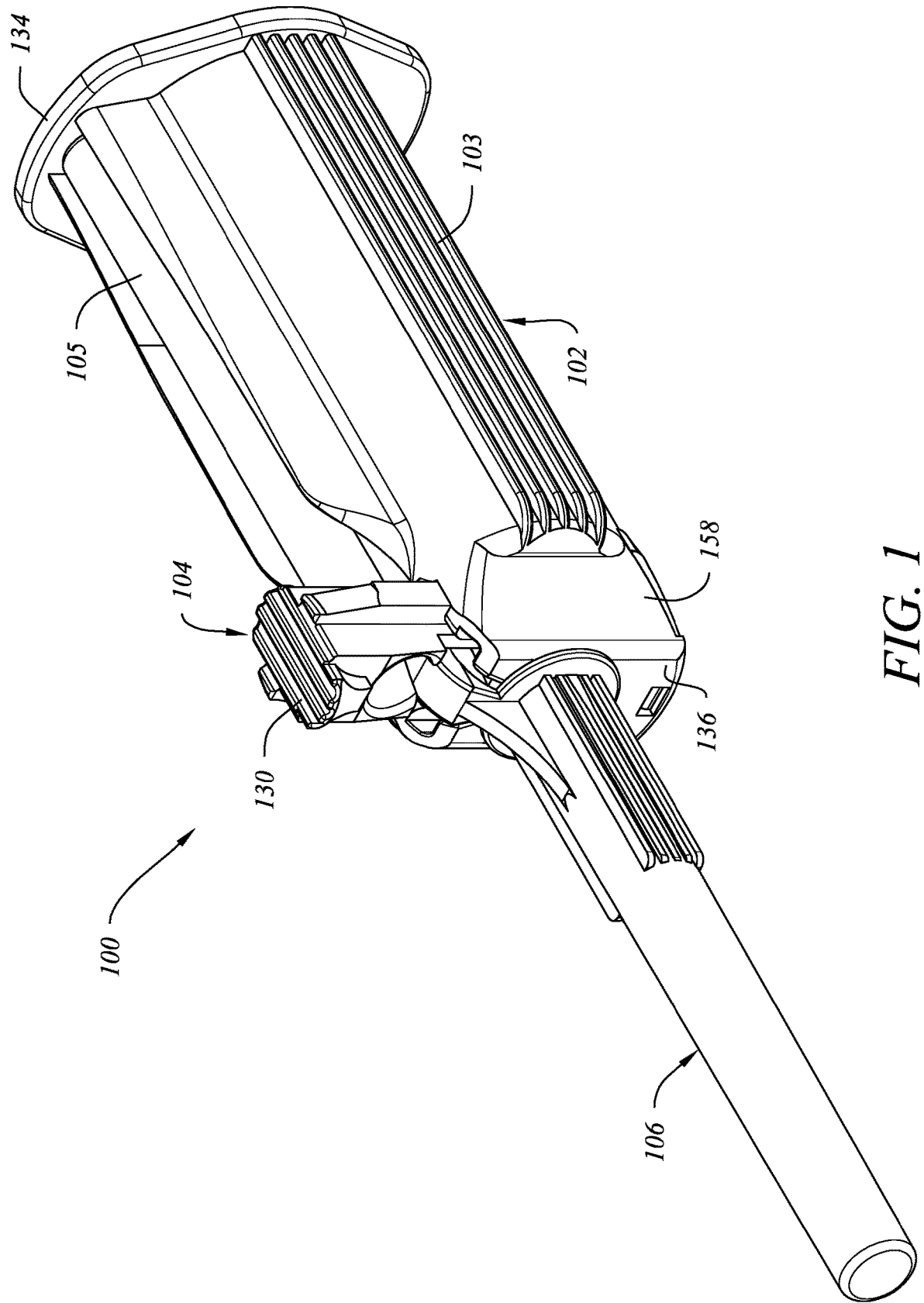
FIG. 1 is a top front perspective view of one embodiment of a medical device of the invention with a locking cap installed on the device.
Figure 2:
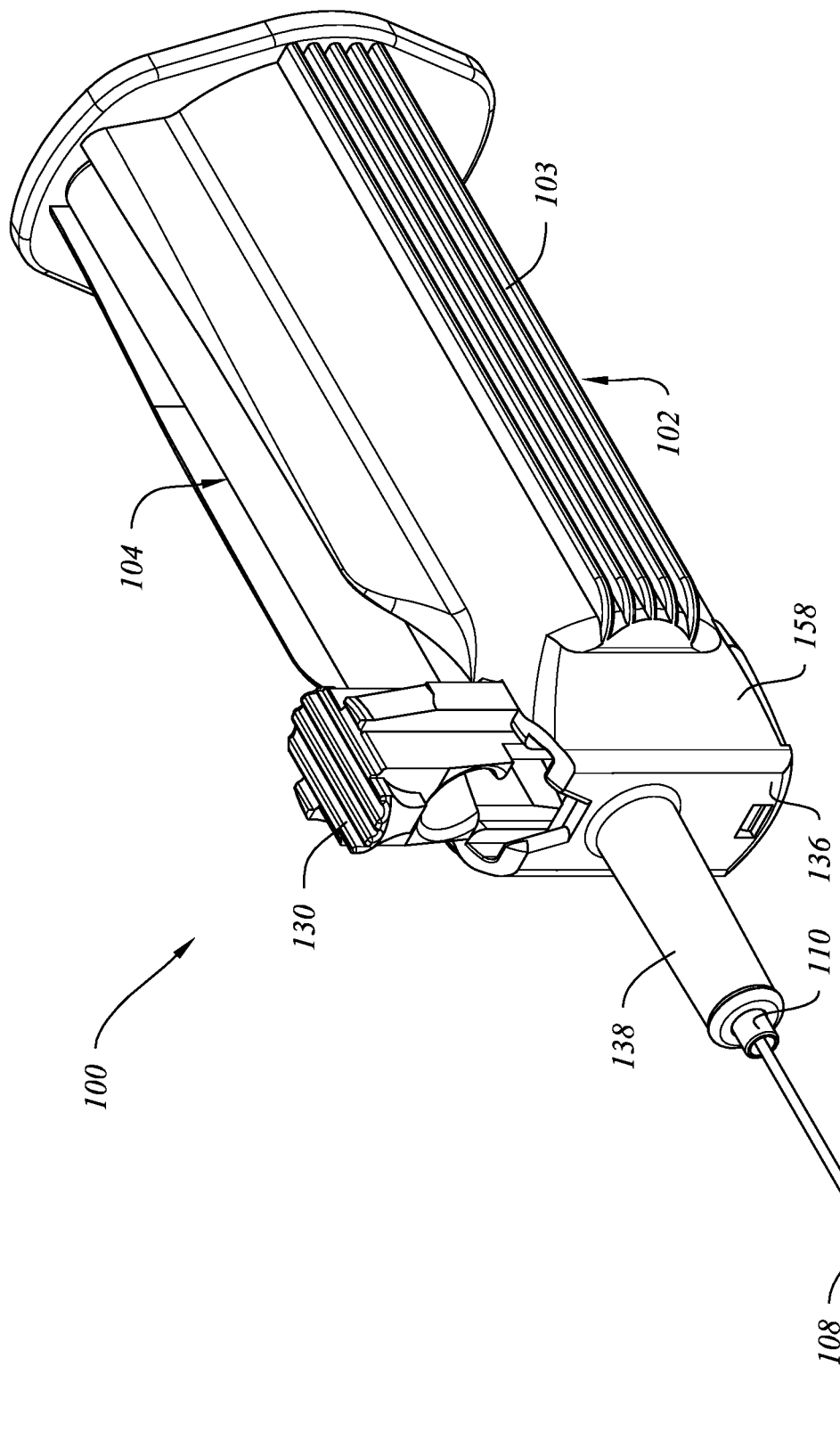
FIG. 2 is a top front perspective view as in FIG. 1 but with the locking cap removed.

Referring to FIG. 1, blood collection tube holder 100 satisfactorily comprises body 102, discharge needle displacement member 104 and removable needle cap 106. Body 102 further comprises front wall sections 136, 158, outwardly projecting rear flange 134, and optional textured gripping surfaces 103, 101 (with 101 being visible in FIG. 4). Discharge needle displacement member 104 desirably comprises outwardly facing textured touch surface 130 and rearwardly projecting needle retraction chamber 105. Referring to FIG. 2, removable needle cap 106 of FIG. 1 is removed to reveal forward projecting venipuncture needle 108 held by needle holder 110 seated inside nose 138 of body 102 in addition to parts already mentioned in relation to FIG. 1.

Figure 3:
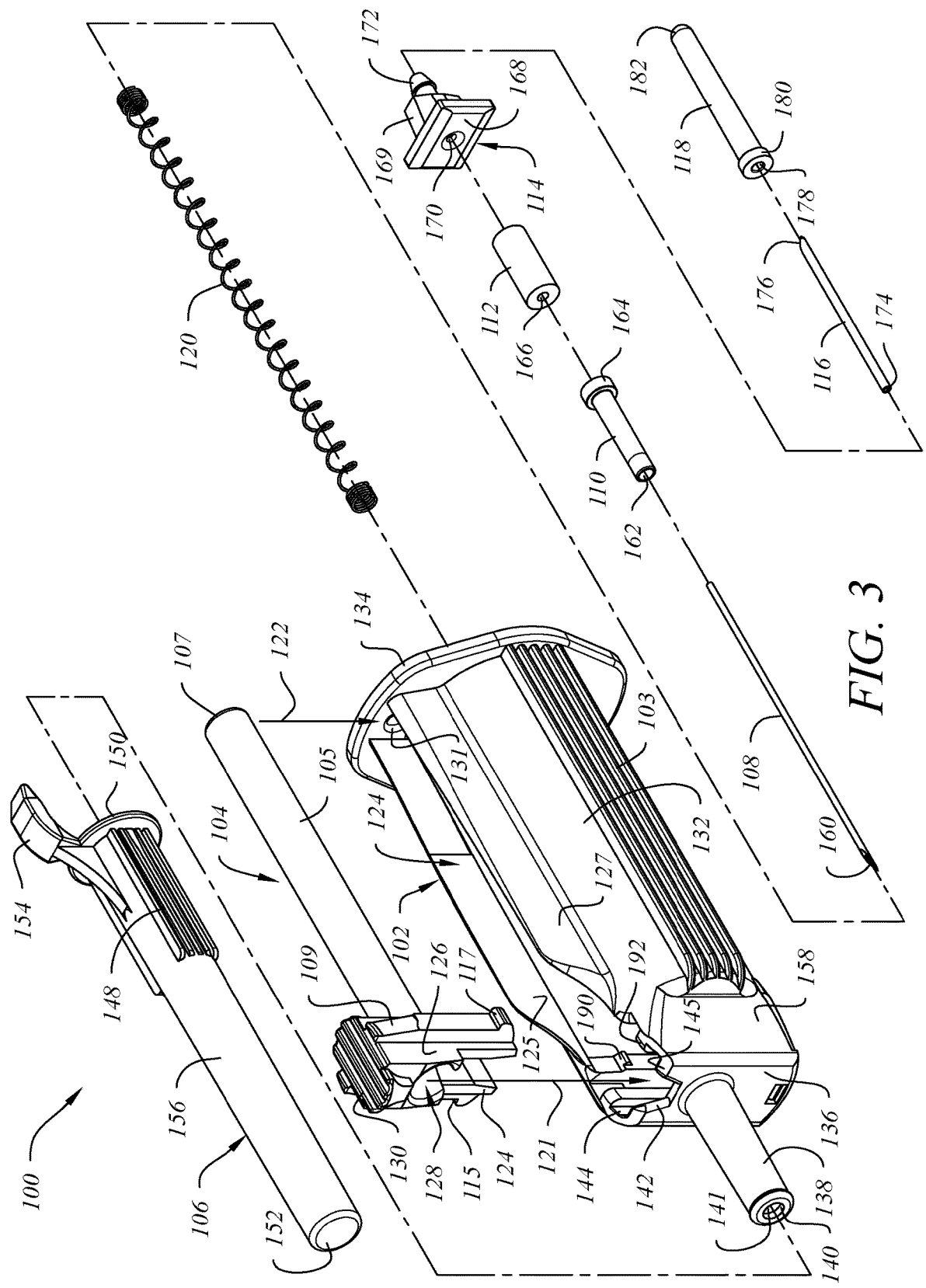
FIG. 3 is an exploded top front perspective view of the medical device of FIG. 1.

Referring to FIG. 3, removable needle cap 106 further comprises opposed textured gripping surfaces 148, tapered cylindrical body 156 having closed front end 152 and rear flange 150, and rearwardly projecting, selectively releasable locking arm 154. Body 102 further comprises substantially cylindrical outside wall 132, an elongate opening 124 disposed between longitudinally extending wings 125, 127, guide structures 144, 145 disposed behind front wall 136, and front opening 140 into interior passage 141 inside nose 138. Notch or recess 142 is provided in front wall 136 of body 102 to provide clearance for releasable locking arm 154 of removable needle cap 106. Recess or orifice 131 is optionally provided in the forwardly facing surface of flange 134 between wings 125, 127 for use in releasably engaging and supporting rearwardly facing end 107 of needle retraction chamber 105 as further discussed below in relation to FIG. 4.

Still referring to FIG. 3, the front portion of discharge needle displacement member 104 further comprises front opening 128 that facilitates access into needle retraction chamber 105, and opposed arms 124, 126 that are slidably engageable with cooperatively sized and configured guide structures 144, 145 disposed behind front wall 136 of body 102. Latches 115, 117 on opposed arms 124, 126 are configured to slide past opposed shoulders inside the front portion of body 102 during installation of discharge needle displacement member 104 inside body 102 during assembly of blood collection tube holder 100 as indicated by arrows 121, 122.

Also disposed inside body 102 of blood collection tube holder 100 are compression spring 120 (depicted in expanded condition prior to compression), venipuncture needle 108 having a forwardly projecting beveled end 160 and an opposed blunt end that is insertable into axial bore 162, where it can be held in place by a UV-curable adhesive or by any other similarly effective conventional means. During assembly of blood collection tube holder 100, spring 120 is desirably seated inside nose 138 and is disposed around venipuncture needle 108 and the shaft portion of needle holder 110, and is constrained behind larger diameter head portion 164 of needle holder 110.

Body 102 of blood collection tube holder 100 also comprises needle holder 114 for rearwardly facing fluid discharge needle 116. Needle holder 114 is desirably configured with a front portion 168 that slidably engages guide members 144 behind front wall 136 of body 102 and further comprises intermediate portion 169, rearwardly projecting portion 172 and centrally disposed longitudinal bore 170 that is desirably coaxially aligned with needle holder 110. Forwardly facing end 174 of fluid discharge needle 116 is desirably inserted into bore 170 and is held in place by a UV-curable adhesive or another similarly effective conventional means. Rearwardly facing tip 176 of needle 116 is desirably configured to penetrate the stoppered end of a conventional blood collection tube (not shown) when the blood collection tube is inserted through the opening defined by rear flange 134 of body 102 and into cylindrical cavity 133 inside body 102 (visible in FIGS. 4 and 6) prior to use. Collapsible elastomeric sheath 118 is substantially cylindrical and comprises open end 178 communicating with an internal bore and close end 182. Collar 180 is provided for use in frictionally attaching sheath 118 to rearwardly projecting portion 172 and holds collapsible sheath 118 in position behind intermediate portion 169. Collapsible sheath 118 is desirably long enough to cover rearwardly facing tip 176 of fluid discharge needle 116 prior to use and is collapsed and pushed forward around needle 116 after tip 176 penetrates closed end 182 as it is inserted into the stoppered end of a blood collection tube.

Figure 6:
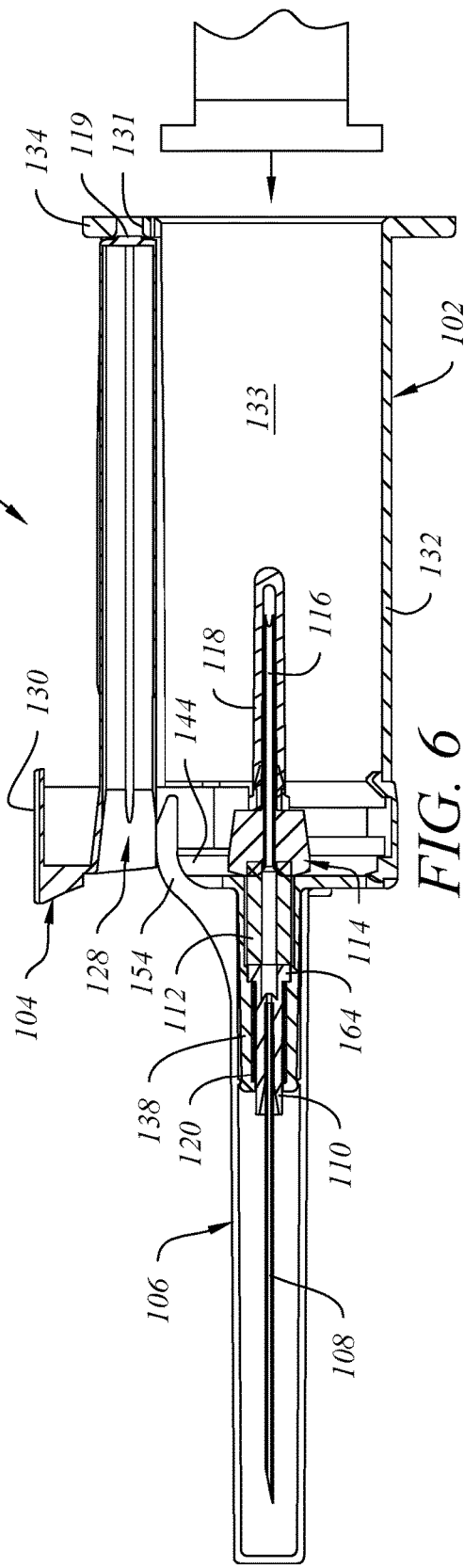
FIG. 6 is a cross-sectional view taken along line 6-6 of FIG. 5.

Referring to FIGS. 3 and 6, compressible fluid seal 112 is substantially cylindrical and has centrally disposed bore 166 that is coaxially aligned with the fluid flow path through needle holders 110, 114. During assembly of body 102 of blood collection tube holder 100, larger diameter head portion 164 is desirably pressured forwardly inside nose 138 of body 102 to compress spring 120, and is held in nose 138 while the front end of compressible fluid seal 112 is inserted into nose 138 behind needle holder 110. The rear end of compressible fluid seal 112, which extends rearwardly from nose 138, is then desirably compressed sufficiently to enable needle holder 114 to be slidably inserted into body 102 behind compressible fluid seal 112 to establish fluid-tight engagement between compressible fluid seal 112 and each of needle holders 110, 118. The relative positions of nose 138, needle holders 110, 114 compressible fluid seal 112 as assembled inside body 102 are better seen in FIG. 6.

Figure 4:
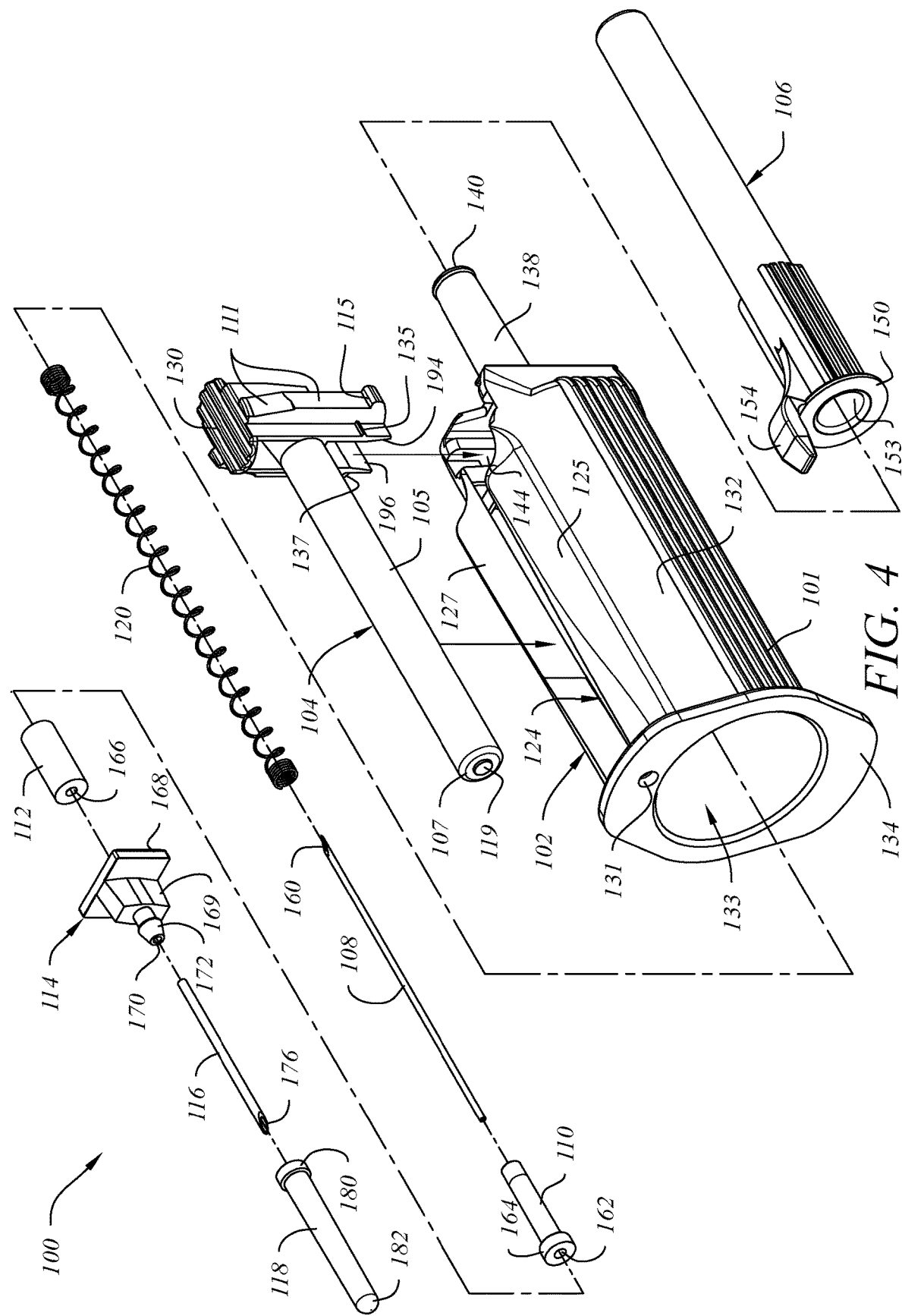
FIG. 4 is an exploded top rear perspective view of the medical device of FIG. 1.

Referring to FIG. 4, like reference numerals are used to identify parts of blood collection tube holder 100 already discussed above in relation to FIG. 3. Additional structural elements not visible in FIG. 3 include inside bore 153 of removable needle cap 106, textured gripping surface 101 (visible in FIG. 5 opposite textured gripping surface 103), and optional rearwardly facing projection 119 of discharge needle displacement member 104 that is aligned with aperture 131 when discharge needle displacement member 104 is installed inside body 102 as shown in FIG. 6. It should be understood that projection 119 and aperture 131 are merely illustrative of other similarly effective structures that can optionally provide releasable frictional engagement between the closed rear end of discharge needle displacement member 104 and outwardly projecting rear flange 134. Where present, projection 119 and aperture 131 are desirably cooperatively sized and aligned to form a releasable frictional engagement mechanism that provides additional support to the rear end of discharge needle displacement member 104 prior to and during use of blood collection tube holder 100 to collect a blood sample. Projection 119 desirably remains in releasable engagement with aperture 131 until discharge needle displacement member 104 is moved into contact with needle holder 114 inside body 102 following withdrawal of a blood collection tube from cylindrical cavity 133 (FIG. 6) inside body 102.

Figure 5:
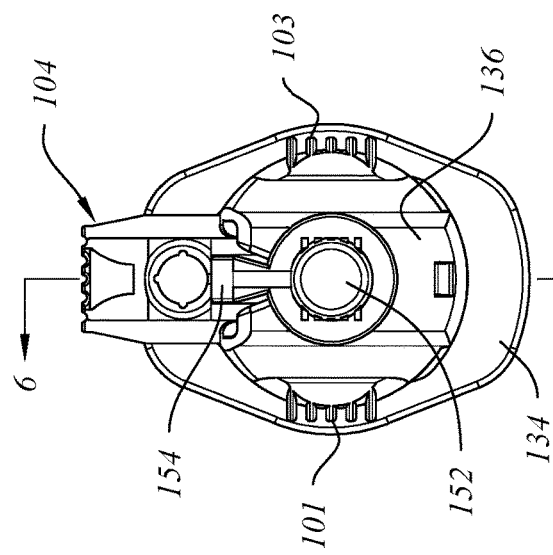
FIG. 5 is a front elevation view of the medical device of FIG. 1.

Referring to FIGS. 5 and 6, blood collection tube holder 100 of the invention as described in relation to FIGS. 1, 3 and 4 is shown in fully assembled form with removable needle cap 106 installed as shown in FIG. 1, and with releasable locking arm 154 inserted into body 102. When disposed in the position shown, releasable locking arm 154 supports and prevents the front portion of discharge needle displacement member 104 from being inadvertently moved further inwardly into body 102 during shipping and storage, and prior to removal of needle cap 102 prior to use. As depicted in FIG. 6, a continuous fluid flow path extends from venipuncture needle 108 thorough needle holder 110, compressible fluid seal 112 and needle holder 114 to fluid discharge needle 116, all of which are desirably coaxially aligned for use in drawing a blood sample after removal of needle cap 106 and insertion of a blood collection tube into blood collection tube holder 100.

Referring to FIGS. 3, 4, 7 and 8, structures are disclosed that are exemplary of a variety of different structures that can be used by one of ordinary skill in the art upon reading this disclosure to position and support discharge needle displacement member 104 relative to body 102 (as viewed from the rear through the opening defined by flange 134) even after releasable locking arm 154 is withdrawn from its locking position beneath discharge needle displacement member 104 following removal of needle cap 106. Looking first at FIGS. 4 and 7, rearwardly facing projection 119 of needle retraction chamber 105 is aligned with and releasably inserted into a recess or aperture 131 of flange 134. Looking next at detail view of FIG. 8 with reference to FIGS. 3, 4 and 7, as discharge needle displacement member 104 is inserted into body 102, free ends 194, 196 of arms 124, 126, respectively, slide past inwardly facing tapered shoulders 190, 192 of guide members 144, 145 behind front portion 168 and beside intermediate portion 169 of needle holder 114 (FIGS. 3 and 4) until the tapered portions of shoulders 135, 137 of arms 124, 126, respectively, contact and rest against inwardly facing tapered shoulders 190, 192. FIGS. 7 and 8 indicate the resting position of discharge needle displacement member 104 relative to body 102 prior to and during use of the device to draw a blood sample.

Figure 11:
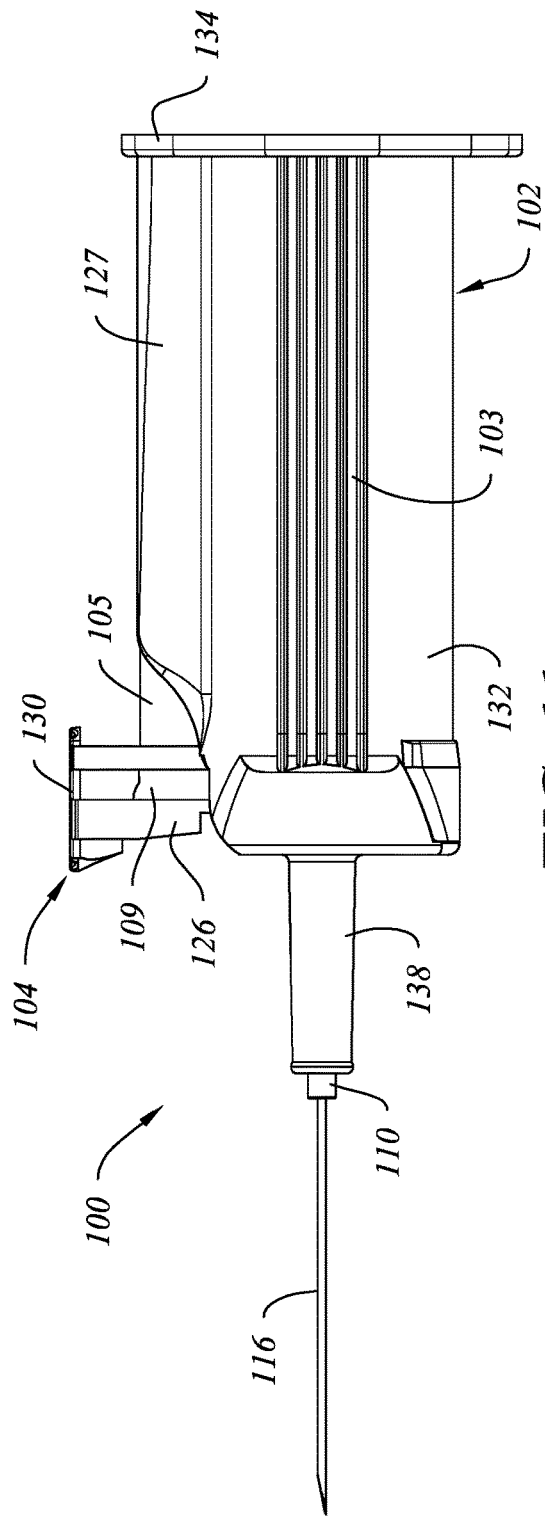
FIG. 11 is a side elevation view of the device of FIG. 2.
Figure 12:
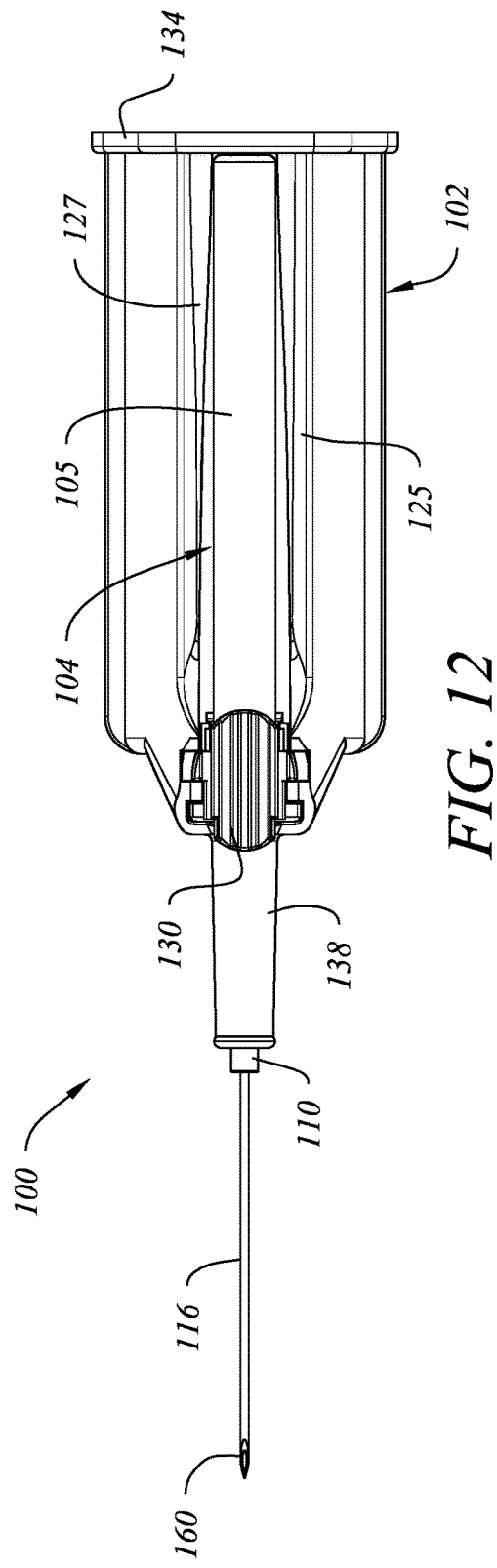
FIG. 12 is a top plan view of the device of FIG. 2.
Figure 17:
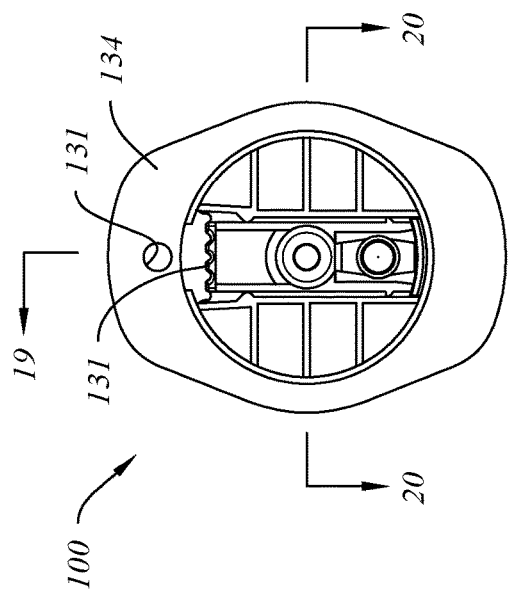
FIG. 17 is a rear elevation view of the device as depicted in FIG. 15.
Figure 18:
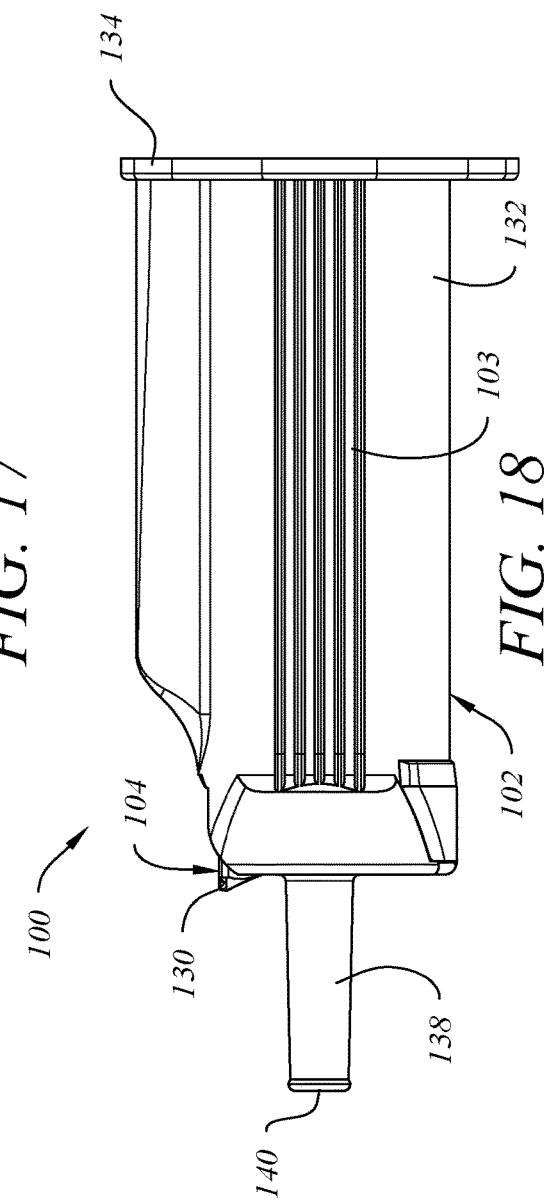
FIG. 18 is a side elevation view of the device as depicted in FIG. 15.

Referring to FIGS. 9 and 10, a transverse cross-sectional view is taken behind front wall 136 of body 102 to better illustrate the positions of discharge needle displacement member 104 and opening 128 into needle retraction chamber 105 relative to body 102 prior to and during use of the device but prior to retraction of the venipuncture needle. As best seen in FIG. 10, when support arms 109, 111 of discharge needle displacement member 104 are installed in body 102, hook members 115, 117 disposed at the lower ends of support arms 111, 109, respectively, are initially flexed inwardly and then pass opposing square shoulders in walls 202, 204 of guide structures 144, 145, respectively, that permit movement in the direction of arrows 198, 200 (which movement is still restricted by the resistance imposed by tapered shoulders 190, 192 as discussed above in relation to FIG. 8) but prevent movement in the opposite direction to disengage discharge needle displacement member 104 from body 102. FIGS. 11 and 12 disclose two additional orthogonal views of blood collection tube holder 100 with venipuncture needle 116 projecting forwardly from needle holder 110 and nose 138, and with discharge needle displacement member installed in the use position relative to body 102. Other reference numerals used in FIGS. 11 and 12 are consistent with those previously described in relation to other drawing figures.

Following use of blood collection tube holder 100, as manual pressure is applied to textured touch surface 130 (FIG. 7), free ends 194, 196 are squeezed together by the tapered surfaces of shoulders 135, 137 sliding downwardly past inwardly facing shoulders 190, 192 of guide structures 144, 145, respectively. Once shoulders 135, 137 move past shoulders 190, 192, the front portion of discharge needle displacement member 104 is no longer constrained in the pre-use and use position. The same manual force applied to textured touch surface 130 is desirably sufficient to overcome the frictional holding force between projection 119 and aperture 131. This causes projection 119 to disengage from aperture 131 and allows both the front and rear portions of discharge needle displacement member 104 to move inwardly relative to body 102. As this movement occurs, the front portion of discharge needle displacement member 104 contacts needle holder 114 (FIG. 4) and displaces needle holder 114 and fluid discharge needle 116 laterally away from compressible fluid seal 112, simultaneously disrupting the continuous fluid flow path that existed between venipuncture needle 108 and fluid discharge needle 116 (FIG. 6) prior to the contact and displacement.

FIGS. 13 and 14 depict cross-sectional views similar to those previously described in relation to FIGS. 9 and 10 except that the section is taken through front portion 168 of needle holder 114 and the needle retraction process has been initiated. As shown, discharge needle displacement member 104 is moved out of engagement with aperture 131 in flange 134 of body 102, and the front portion of discharge needle displacement member 104 is moved into contacting and abutting relation with the top of front portion 168 of needle holder 114. From this position, continued application of manual pressure to textured touch surface 130 will force discharge needle displacement member 104 into the position shown in FIGS. 15-18, wherein venipuncture needle 108 is fully retracted inside body 102 of blood tube collection holder 100, front portion 168 of needle holder 114 is disengaged from the rear end of compressible fluid seal 112, and needle holder 114 and fluid discharge needle 116 are forced into the position best shown and further described below in relation to FIGS. 19 and 20.

Referring to FIGS. 19 and 20, when discharge needle displacement member 104 is moved to the position shown, needle retraction chamber 105 becomes coaxially aligned with collapsible fluid seal 112, needle holder 110 and venipuncture needle 108, all of which are then propelled by expanding compression spring 120 into needle retraction chamber 105. When disposed in this position, venipuncture needle 108 is no long exposed in a position where accidental needle stick injuries and related contamination by blood-borne pathogens can occur. This is particularly true if venipuncture needle 108 is retracted directly from the body of a patient as recommended. At the same time, needle holder 114 and fluid discharge needle 116, together with any fluid remaining inside them, are confined between the back side of front wall 136 and the closed rear end 182 of collapsible elastomeric sheath 118 that is preferably substantially impermeable to any blood remaining inside fluid discharge needle 116.

Other alterations and modifications of the invention disclosed here will likewise become apparent to those of ordinary skill in the art upon reading this specification and claims in relation to the accompanying drawings, and the inventors intend that the scope of the invention be limited only by the broadest interpretation of the appended claims to which the inventors are legally entitled.

We claim:

1. A blood collection tube holder configured for use with a stoppered blood collection tube to draw and collect blood, the blood collection tube holder comprising:
   a molded plastic body having front wall sections, a body wall extending rearward from the front wall sections, an elongate opening disposed between longitudinally extending wings disposed on the body wall, a cylindrical cavity inside the body, and a rearwardly facing opening surrounded by an outwardly projecting, laterally extending rear flange disposed on the body wall;
   two spaced-apart, oppositely facing, coaxially aligned needles held inside the body, wherein the first needle is a forwardly projecting venipuncture needle held by a rearwardly biased needle holder and the second needle is a rearwardly facing fluid discharge needle held by a second needle holder; and
   a discharge needle displacement member slidably engaging the body and further comprising a rearwardly projecting needle retraction chamber and a touch surface,
   wherein the discharge needle displacement member is selectively repositionable, following use of the blood collection tube holder to draw and collect blood, in a direction transverse to a fluid flow path through the blood collection tube holder by an application of manual pressure to the touch surface to displace the fluid discharge needle laterally relative to the venipuncture needle and to coaxially align the rearwardly biased needle holder with the needle retraction chamber to initiate retraction of the venipuncture needle;
   wherein the needle retraction chamber comprises a rearwardly facing closed end, and
   wherein the laterally extending flange and the closed end of the needle retraction chamber are cooperatively configured to be releasably engageable with each other prior to and during use of the blood collection tube holder to draw and collect blood.

2. The blood collection tube holder of claim 1 wherein the closed end of the needle retraction chamber releasably engages the laterally extending flange.

3. The blood collection tube holder of claim 2 wherein the closed end of the needle retraction chamber comprises a rearwardly facing projection that releasably engages a cooperatively sized and aligned aperture in the laterally extending flange.

* * * * *